United States Patent [19]
Franklin et al.

[11] Patent Number: 6,017,557
[45] Date of Patent: *Jan. 25, 2000

[54] CARRIERS CONTAINING AN ETHERLIPID/COMPLEMENTARILY SHAPE LIPID COMBINATION AND THERAPEUTIC USES THEREOF

[75] Inventors: J. Craig Franklin, Skillman; Eric Mayhew, Monmouth Junction; Walter Perkins, Hopewell Township, all of N.J.; Andrew Janoff, Yardley, Pa.

[73] Assignee: The Liposome Company, Inc., Princeton, N.J.

[ * ] Notice: This patent is subject to a terminal disclaimer.

[21] Appl. No.: 08/950,773

[22] Filed: Oct. 15, 1997

Related U.S. Application Data

[63] Continuation-in-part of application No. 08/720,997, Oct. 15, 1996, Pat. No. 5,932,242.

[51] Int. Cl.$^7$ .................................................. A61K 9/127
[52] U.S. Cl. ........................................ 424/450; 428/402.2
[58] Field of Search ........................... 424/450; 436/829; 428/402.2

[56] References Cited

U.S. PATENT DOCUMENTS

| | | | |
|---|---|---|---|
| 3,752,886 | 8/1973 | Munder et al. | 424/199 |
| 4,426,525 | 1/1984 | Hozumi et al. | 546/22 |
| 4,734,225 | 3/1988 | Eibl | 260/386 |
| 4,804,789 | 2/1989 | Eibl | 568/853 |
| 4,965,391 | 10/1990 | Counsell et al. | 558/169 |
| 4,983,397 | 1/1991 | Schroit et al. | 424/450 |
| 5,077,057 | 12/1991 | Szoka et al. | 436/829 |
| 5,169,637 | 12/1992 | Lenk et al. | 514/192 |

FOREIGN PATENT DOCUMENTS

| | | |
|---|---|---|
| 4132345 | 4/1993 | Germany . |

OTHER PUBLICATIONS

Bazill, et al., "Role of Endocytosis in the Action of Eher Lipids on WEHI–3B, HL60, and FDCP–Mix A4 Cells", Cancer REsearch, 50, 7505–7512, Dec. 1, 1990.
Berdel, "Ether Lipids and Derivatives as Investigational Anticancer Drugs", Onkologie 1990: 13:245–250.
Bhatia, et al., "Stereospecific Synthesis of Antitumor Active Thioether PAF Analogs", Lipids, 26(12), 1424–1430, 1991.
Chen, et al., "Microdetermination of Phosphorus", Anal. Chem., 28 (110), 1756–1758; 1956.
Deamer, et al., "Liposome Preparation: Methods and Mechansims", in Liposomes, Marcel Dekker, ed. M. Ostro, 1983, 27–51.
Dietzfelbinger, et al., "Removal of Breast Cancer Cells from Bone Marow by in Vitro Purging with Ether Lipids and Cryopreservation", Cancer Research 53, 3747–3751, Aug. 15, 1993.
Gruner, "Nonlamellar Lipis Phases", in *The Structure of Biological Membranes,* 1992, CRC Press, ed. P. Yeagle, Buffalo, NY, pp. 222–223.

Kumar, et al., "Phosphlipid Deitribution and Headgroup Motion in Phosphatidylcholine Liposomes of Different Size", Biophys. J., 53, 1988, 121a.
Layton, et al., "The Interaction of Liposomes with Cells: The Relation of Cell Specific Toxicity to Lipid Composition", Eur J Cancer, 16, 1529–1538, 1980.
Madden, et al., "Stabilization of bilayer Structure for Unsaturated Phosphatidylethanolamines by Detergents", BBA, 684(1982), 149–153.
Nairn, et al., "Solutions, Emulsions, Suspensions and Extractives", in *Pharmaceutical Sciences,* 1985, Mack Publishing Co., Easton, PA.
Papahadjopoulos, et al. "Phospholipid Model Membranes, I. Structural Characteristics of Hydrated Liquid Crystals", BBA 135 (1967) 624–638.
Powis, et al., "Selective Inhibition of Phosphatidyloinositol Phospholipase C by Cytotoxic Ether Lipid Analogues", Cancer Research 52, 2835–2840, May 15, 1992.
Reed, et al., "Antineoplastic Ether–Linked Phospholipid Inudces Differentiation of Acute Myelogenous Leukemic KG–1 Cells Into Macrophase–Like Cells", Life Sciences, 49, 1221–1227, 1991.
Runge, "Destruction of human Solid tumors by Alkyl Lysophospholipids", JNCI, 64(6), Jun. 1980, 1301–1306.
Tritton, et al., "How to Kill Cancer Cells: Membranes and Cell signaling as Targets in Cancer Chemotherapy", Cancer Cells, Apr. 1990, 95–105.
Stedman's Medical Dictionary, pp. 707–708.
Stedman's Medical Dictionary, pp. 123–124.
Workman, "Antitumor Ether Lipids: Endocytosis as a Determinant of Cellular Sensitivity", Cancer Cells, 3(8), 315–317, Aug. 1991.
Workman, et al., "Platelet–activating factor (PAF) antagonist WEB 2086 does not modulate the cytotoxicity of PAF or antitumour alkyl lysophospholipids ET–18–O–Methyl and SRI 62–834 in HL–60 promyelocytic leukaemia cells", Biochemical Pharmacology, 41(2), 319–322, 1991.
Wu, et al., "Modified In Vivo behavior of Liposomes Containing Synthetic Glycolipids", BBA 674 (1981), 19–29.
Zeisig, et al., "Antineoplastic activity in vitro of free an liposomal alkylphosphocholines", Anti–Cancer Drugs, 4, 57–64, 1993.

*Primary Examiner*—Mary E. Ceperley
*Attorney, Agent, or Firm*—Rosanne Goodman

[57] ABSTRACT

Lipid-based carriers are provided herein that have a lamellar lipid component composed of an etherlipid and a complementarily shaped lipid. This novel combination of lipids allows for the incorporation of etherlipids in the carriers at higher concentrations than would otherwise be possible. Pharmaceutical compositions containing the carriers can be used therapeutically, for example, in the treatment of cancers.

18 Claims, 5 Drawing Sheets

CARRIERS CONTAINING AN ETHERLIPID/COMPLEMENTARILY SHAPE LIPID COMBINATION AND THERAPEUTIC USES THEREOF

This application is a continuation-in-part of application Ser. No.08/720,997, filed Oct. 15, 1996, now U.S. Pat. No. 5,932,242.

FIELD OF THE INVENTION

This invention is directed to ether lipid-containing pharmaceutical compositions, and to the use of such compositions in the treatment of various disorders, e.g., cancer and inflammatory conditions.

BACKGROUND OF THE INVENTION

Cancer chemotherapy generally aims to slow the growth of, or destroy, cancer cells while avoiding collateral damage to surrounding cells and tissues; the most effective anticancer agents are thus those that are best able to selectively target cancer cells while leaving normal cells relatively unaffected.

Ether lipids can be effective as anticancer agents (see, for example, Dietzfelbinger et al. (1993); Zeisig et al. (1993); Powis et al. (1990); Berdel (1991); Bhatia and Hadju (1991); Reed et al. (1991); Workman (1991); Workman et al. (1991); Bazill and Dexter (1990); Berdel (1990); Counsell et al. (1990); Tritton and Hickman (1990); Muschiol et al. (1990); Layton et al. (1980); Runge et al. (1980); Munder & Westphal (1990); Lohmeyer & Workman (1995); Lohmeyer & Biftman (1994); Great Britain Patent No. 1,583,661; U.S. Pat. No. 3,752,886). Several mechanisms of action have been proposed for the toxicity of etherlipids towards cancer cells, including the cells' lack of alkyl cleavage enzymes; the resultant inability to hydrolyze the etherlipids leads to their intracellular accumulation and to consequent damage to cell membrane lipid organization. Other potential mechanisms of etherlipid action include effects on levels of intracellular protein phosphorylation, and disruption of cellular lipid metabolism.

Normal cells typically possess the means to avoid or overcome the potentially toxic effects of etherlipids, while cancer cells do not. However, normal cells, e.g., red blood cells ("RBCs"), which do not possess such means are subject to the same disruptive effects of etherlipid action as are cancer cells. In fact, hemolysis resulting from exposure of RBCs to etherlipids has been found to be a significant impediment to the therapeutic use of the etherlipids (see, for example, Houlihan et al., 1995). One approach to solve this problem of etherlipid-induced cytotoxicity is to incorporate the drugs into lipid-based carriers, e.g., liposomes.

This invention provides a lipid-based carrier having a lamellar lipid component that contains the etherlipid and a lipid of complementary molecular shape to the etherlipid; this shape complementarity allows etherlipids to be incorporated into the lipid-based carriers at higher concentrations than would otherwise be possible. The novel combination of the etherlipids and complementarily shaped lipids in the pharmaceutical compositions of this invention has not previously been described. PCT/US95/12721 describes liposomes containing cholesterol, a phosphatidylcholine and a phosphatidylethanolamine-dicarboxylic acid derivative, in addition to a glycerol-based ether lipid having a methoxy group attached to the second position of the glycerol backbone. German Patent Application No. 4,132,345 describes liposomes containing cholesterol and a positively or negatively charged lipid in addition to a methoxy group-containing ether lipid. Japanese Patent Application No. 61-022,020 describes liposomes containing cholesterol and a phospholipid in addition to an acetyl, or propionyl, group-containing glycerol-based ether lipid. Mende et al. describes the membrane potential altering effects of liposomes containing an ether lipid/cholesterol combination of an equimolar ratio. However, none of these documents describes pharmaceutical compositions containing complementarily shaped lipids and glycerol-based ether lipids having a methoxy group at the second position.

SUMMARY OF THE INVENTION

Etherlipids are known to be effective anticancer agents; however, they are also known to be cytotoxic to some normal cells as well. Accordingly, efficient therapeutic use of etherlipids requires a means of delivering etherlipids' such that their toxicity is buffered while their therapeutic potential is maintained. This invention provides such a means, in the form of a lipid-based carrier having a lamellar lipid component which comprises an ether linkage-containing glycerolipid, i.e., an "ether lipid," and a "complementarily shaped lipid," i.e., a lipid having a shape that is complementary to the molecular shape of the ether lipid. The glycerolipid has the formula:

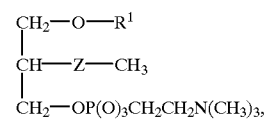

wherein $R^1$ is preferably a group having the formula $-(CH_2)_{n1}CH_3$, and more preferably is $-(CH_2)_{17}CH_3$; Z is preferably oxygen. Most preferably, the glycerolipid is therefore:

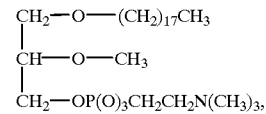

i.e., "ET-18-OCH$_3$" or (C-18 etherlipid).

The complementarily shaped lipid is preferably selected from the group consisting of a neutral sterol, a neutral sterol/anionic sterol combination, cardiolipin, di- and triacylglycerol, diarachidonoyl phosphatidylethanolamine ("DAPE") or a similar lipid. More preferably, the complementarily shaped lipid is cholesterol, cholesterol sulfate or a combination of cholesterol and cholesterol sulfate.

Pharmaceutical compositions containing the carriers of this invention can be used therapeutically, for example, to reduce the size of tumors in mammals, by administering to the mammals an amount of a composition which comprises a therapeutically effective amount of the glycerolipid.

DETAILED DESCRIPTION OF THE INVENTION

This invention provides lipid-based carriers having lamellar lipid components which comprise complementarily shaped lipids and lipids having a three-carbon glycerol backbone, i.e., "glycerolipids." These glycerolipids comprise a hydrocarbon chain ("R$_1$"), the terminal methylene carbon of which is linked to the glycerol backbone at position number 1 of the backbone through an oxygen atom. Hence, the hydrocarbon chain is connected to the glycerol backbone by way of an ether linkage, and the glycerolipids of this invention are "ether linkage-containing" glycerolipids or "ether lipids." A methyl group is linked to the glycerol backbone at position number 2 of the glycerol backbone, through either an oxygen atom or a sulfur atom, and a phosphorylcholine group (—OP(O)$_3$CH$_2$CH$_2$N(CH$_3$)$_3$) is attached at position number 3. Accordingly, the glycerolipid of this invention has the following general structural formula, as either the L- or D-isomer, although the L-isomer is presently preferred:

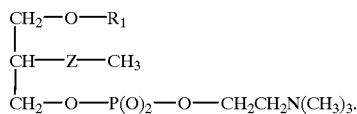

R$^1$ is a group having the formula Y$^1$Y$^2$, wherein Y$^1$ is the group —(CH$_2$)$_{n1}$(CH=CH)$_{n2}$(CH$_2$)$_{n3}$(CH=CH)$_{n4}$(CH$_2$)$_{n5}$(CH=CH)$_{n6}$(CH$_2$)$_{n7}$(CH=CH)$_{n8}$(CH$_2$)$_{n9}$. The sum of n1+2n2+n3+2n4+n5+2n6+n7+2n8+n9 is an integer of from 9 to 23; n1 is zero or an integer of from 1 to 23, n3 is zero or an integer of from 1 to 20, n5 is zero or an integer of from 1 to 17, n7 is zero or an integer of from zero to 14 and n9 is zero or an integer of from 1 to 11; each of n2, n4, n6 and 8 is independently zero or 1. Y$^1$ is preferably saturated, having the formula —(CH$_2$)$_{n1}$CH$_3$ as each of n2, n3, n4, n5, n6, n7 and n8 is then equal to 0. Y$^2$ is C(O)$_2$H or CH$_3$, and is preferably CH$_3$.

R$_1$ is thus preferably —(CH$_2$)$_{n1}$CH$_3$, more preferably —(CH$_2$)$_{17}$CH$_3$. Z is O or S, but is preferably O. Accordingly, the glycerolipid of this invention is preferably:

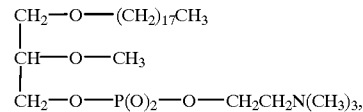

that is, 1-O-octadecyl-2-O-methyl-sn-3-phosphorylcholine (C-18 etherlipid, "EL-18" or "ET-18—OCH$_3$").

Figure 4:
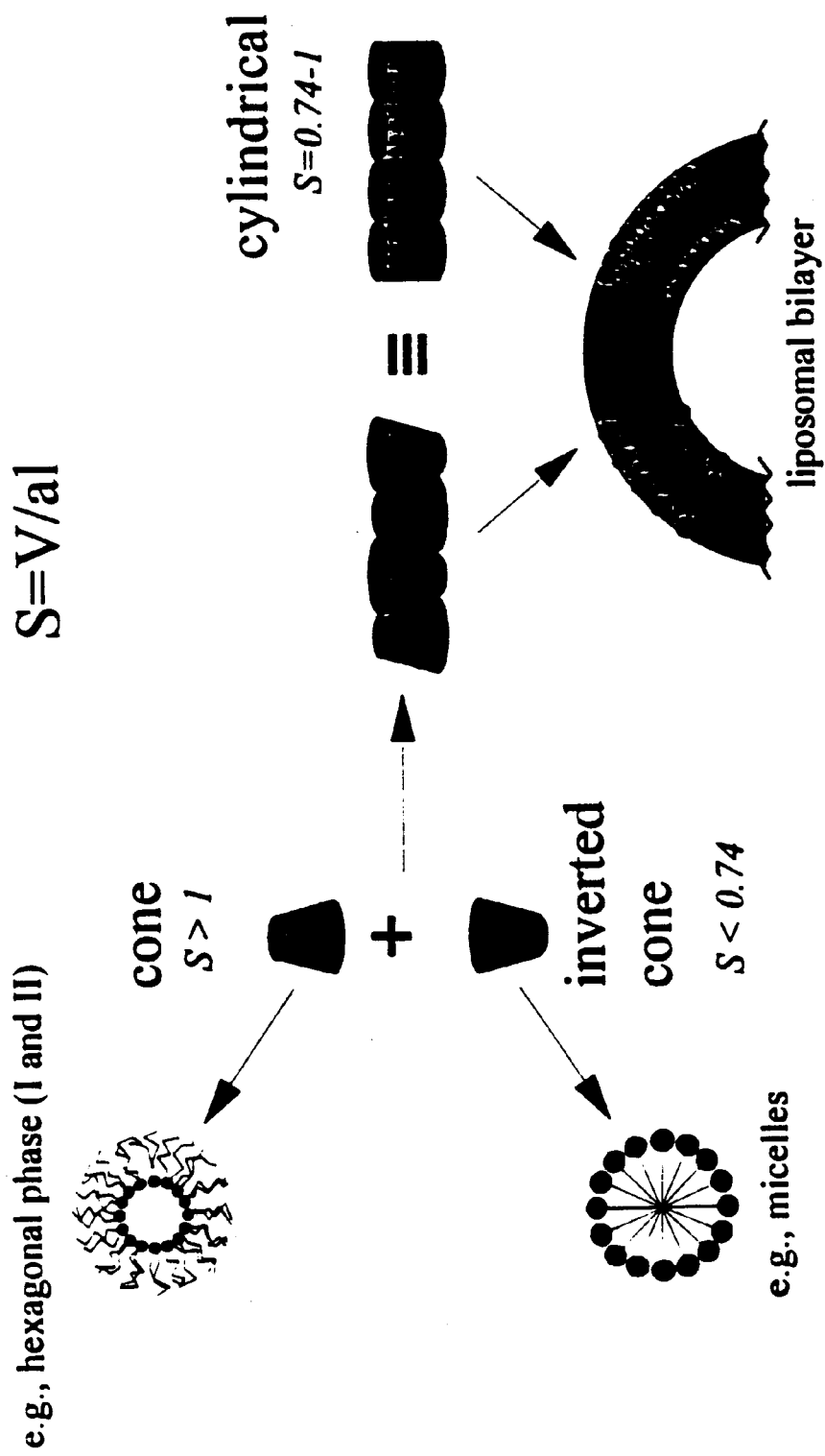
FIG. 4. Schematic representation of the effect of lipid molecular shape on collective organization. Darkened regions represent hydrophilic lipid headgroups; shaded regions represent the lipids' hydrophobic hydrocarbon domains.

In addition to the etherlipid, the lamellar lipid component contains an amphipathic lipid molecule having a molecular shape that is complementary to that of the etherlipid, i.e., a "complementarily shaped lipid." Amphipathic lipids generally have either a cone-shaped, cylindrical or inverted cone-shaped molecular shape in aqueous environments (FIG. 4). The particular shape of a hydrated amphipathic lipid molecule depends upon the relative size of the molecule's polar headgroup and hydrophobic acyl chain domain (see, e.g., Kumar et al., 1991; Rand et al., 1975; Madden & Cullis, 1982; Wu et al., 1991; Wu & Chi, 1991; and, Israelachvili, et al., 1976, the contents of which are incorporated herein by reference).

Cone-shaped lipids have headgroup surface areas that are less than cross-sectional areas of their hydrocarbon domains; these lipids form micelles in aqueous environments, wherein the lipid headgroups are arrayed around the exterior of the micelle while the hydrocarbons are sequestered in the interior. Inverted cone-shaped lipids have headgroup surface areas that are larger than hydrophobic domain cross-sectional areas; these lipids form inverted micelles, wherein the headgroups are arrayed in the structure's interior, and the hydrocarbons are arrayed around the exterior. Cylindrical lipids have headgroup surface areas that are about equal to cross-sectional areas of their hydrophobic domains. These lipids can form bilayers on their own, with their hydrocarbons then being arrayed in a generally planar side-by-side conformation in the bilayer's interior while the lipid headgroups are arrayed towards the surrounding aqueous environment.

Cylindrical lipids are particularly suited to the formation of lamellar structures because of the symmetry they possess along the long axes of their molecules. This symmetry allows the lipids to adopt planar side-by-side conformations in bilayers, an arrangement consistent with the lipids' providing maximal shielding of their hydrophobic hydrocarbons from energetically unfavorable contacts with the surrounding water.

Cone-shaped lipids and inverted cone-shaped lipids, with their disparately sized headgroups and hydrocarbon domains, generally do not form lamellae on their own. The asymmetries of their molecular shapes means that arrangement in a bilayer is not the most efficient arrangement for shielding the lipids' acyl chain regions from contact with the aqueous environment. Side-by-side packing of cone-shaped and inverted cone-shaped lipids in bilayers would, because of the asymmetric molecular shapes, leave significant portions of the lipids' hydrocarbon domains exposed to the aqueous environment. Inverted micelles, for cone-shaped lipids, and micelles, for inverted cone-shaped lipids, expose less of the hydrocarbon regions of these lipids, and hence, are more energetically favorable structures for these types of lipids.

However, combined cone-shaped and inverted cone-shaped lipids can form lamellae, as the combination affords approximate symmetry along the long axes of the combined lipid molecules. Maximum shielding of acyl chain regions from water for approximately equimolar combinations of cone-shaped and inverted cone-shaped lipids is provided by their arrangement in a bilayer structure. Accordingly, a "complementarily shaped lipid" is a lipid having an asymmetric, noncylindrical molecular shape which can, together with a second asymmetrically shaped lipid molecule, form a lipid molecular pair having approximate symmetry along the combined molecules' long axis. Thus, for inverted cone-shaped molecules, such as the glycerolipids of this invention, a complementarily shaped lipid is a cone-shaped lipid.

The relative size of an amphipathic lipid's headgroups and acyl chain regions, and hence, the lipid's molecular shape, can be expressed by the value of the lipid's packing parameter, "S," determined in accordance with the equation $S=V/(a)(l)$ [wherein "V" is the volume of the lipid's hydrocarbon domain, "a" is the lipid's headgroup surface area and "l" is the length of the hydrocarbon chain(s). Cylindrical lipids, with their about symmetrical shape, have a packing parameter of about 0.74–1. Inverted cone-shaped lipids, whose polar regions occupy a relatively larger space than do their hydrophobic domains, have packing parameters of less than about 0.74. Cone-shaped lipids, with their smaller polar regions and relatively larger hydrophobic domains, have packing parameters of greater than about 1. Accordingly, as "complementarily shaped lipids" herein are cone-shaped, as etherlipids have inverted cone shapes, the complementary lipids also have a packing parameter greater than about 1.

A measure of the amount of space occupied by a lipid molecule is also the mean area ("MMAM") that a molecule of the lipid occupies in a monolayer formed of that lipid. MMAM values for various lipids can readily be determined by ordinarily skilled artisans given the teachings of this invention, for example, as set forth in Example 1 below. Briefly, MMAM values can be determined by first forming a monolayer of the lipid on the surface of an aqueous medium contained within a suitable trough, by the drop-wise addition of a solution of the lipid to the surface of the aqueous medium. Lipid solution is continuously added to the medium's surface until the surface pressure commences to increase; the confines of the trough are then decreased, such that surface area is also decreased. Surface pressures for the different surface areas are recorded, and area-vs.-pressure curves compiled. MMAM values are obtained from these curves by extrapolating the steepest portion of the curve to a lipid's surface area at zero pressure.

The mean area occupied by a lipid molecule in a monolayer formed by a combination of cone-shaped and inverted cone-shaped lipids could be calculated according to the equation $A_0 = X^1 \cdot A^1 + X^2 \cdot A^2$ (see Ali et al., the contents of which are incorporated herein by reference), wherein "$A_0$" is the MMAM expected of the lipids in the two component system, $X^1$ and $X^2$ are the relative mole percentages of the lipids in the combination, and $A^1$ and $A^2$ are the measured MMAM values of the individual lipids. Accordingly, the combination of lipids in a two-component monolayer would be expected to result in a mean molecular area per lipid molecule ("$MMAM_{expected}$") reflective of the relative proportions in which each of the constituent lipids is present in the combination. That is, calculated in accordance with the above equation, the MMAM value expected of the lipids would be additive.

However, additivity of MMAM values is not the case when a glycerolipid is combined with a complementarily shaped lipid in the lipid lamellae of this invention. Rather, when the mean molecular area per molecule of the lipid in the lamellae of this invention is actually measured ("$MMAM_{actual}$"), it is found to be at least 20% less than the corresponding $MMAM_{expected}$ value. That is, the mean area occupied by each of the lipid molecules in a glycerolipid/complementarily shaped lipid lamellae of this invention is at least about 20% less than would have been expected based upon the mean molecular areas of the individual lipids, as determined in accordance with the above equation. Accordingly, a "complementarily shaped lipid" is also a lipid which, when combined in a lamella with a glycerolipid in the proportions set forth herein, results in an $MMAM_{actual}$ of the lipids in the lamella that is at least about 20% less than the corresponding $MMAM_{expected}$ value.

Specific complementarily shaped lipids include, without limitation: neutral sterols; anionic sterol derivatives such as phosphate, sulfate and organic dicarboxylic acid salt derivatives; cardiolipin; various phosphatidylethanolamines such as diarachidonoyl phosphatidylethanolamine ("DAPE"); di- and triacylglycerols; similar lipids; and, combinations of these lipids. Additional complementarily shaped lipids can readily be identified by ordinarily skilled artisans given the teachings of this invention, for example, by identifying lipids which are cone-shaped, have packing parameters of greater than about 1, and which afford to the glycerolipid/complementarily shaped lipid combination an $MMAM_{actual}$ value, determined as described herein, that is at least about 20% less than the corresponding $MMAM_{expected}$ value, calculated as described herein.

Preferred complementarily shaped lipids are neutral sterols and combinations of neutral sterols and anionic sterol derivatives, such combinations preferably being at an about 5:1 molar ratio of neutral sterol to anionic sterol derivative. More preferably, the complementarily shaped lipid is either the neutral sterol cholesterol, the anionic sterol derivative cholesterol sulfate or a 5:1 (molar) combination of cholesterol and cholesterol sulfate. Complementarily shaped lipids are preferably combined with glycerolipids in this invention's lamellae such that the lamellar lipid component of the lipid-based carriers contain from about 30 mole percent to less than about 50 mole % glycerolipid, and from greater than about 50 to about 70 mole percent complementarily shaped lipid. More preferably, the combination is about 40 mole percent glycerolipid and about 60 mole percent complementarily shaped lipid. Accordingly, in the most preferred embodiments of this invention, the lipid lamella consists essentially of about 40 mole percent of the glycerolipid ET-18—$OCH_3$ and about 60 mole percent of a complementarily shaped lipid that is cholesterol, cholesterol sulfate or a 5:1 molar ratio combination of cholesterol with cholesterol sulfate.

MMAM values have been calculated and determined (see below, and FIGS. 3A and 3B) for two-component lipid systems containing the glycerolipid ET-18—$OCH_3$ and the lipids palmitoyloleoyl phosphatidylcholine ("POPC"), dioleoyl phosphatidylcholine ("DOPC"), dioleoyl phosphatidylethanolamine ("DOPE") or cholesterol ("CHOL"), at various mole percentages of the two lipids. ET-18—$OCH_3$ combinations with POPC or DOPC exhibit, at most, a 10–15% MMAM reduction, i.e., a 10–15% difference between the MMAM$_{expected}$ value and the corresponding MMAM$_{actual}$, across the range of lipid concentrations examined. ET-18—OCH$_3$/DOPE combinations also exhibit an MMAM reduction of less than about 20%. Thus, neither POPC, DOPC nor DOPE is a complementarily shaped lipid.

However, for combinations of ET-18—OCH$_3$ and cholesterol at ET-1 8—OCH$_3$ concentrations of between about 30 and 50 mole percent, MMAM$_{actual}$, values are more than 20% less than the corresponding MMAM$_{expected}$ values. For example, a 40 mole % ET-18—OCH$_3$/60 mole % CHOL combination exhibits an MMAM reduction of about 35%, while a 50 mole % /50 mole % combination exhibits a 42% MMAM reduction. Accordingly, substitution of cholesterol for DOPE in the lipid combinations, at the same lipid concentration, makes a significant difference to the degree of MMAM reduction obtained. Such differences in MMAM reductions between ET-18—OCH$_3$/CHOL and ET-18—OCH$_3$/DOPE combinations cannot be predicted based on art knowledge of CHOL and DOPE, because both of these lipids are cone-shaped, and both have packing parameters of about 1.2–1.3. Nevertheless, CHOL combines with glycerolipids so as to achieve MMAM reductions of greater than about 20%, while DOPE does not. Hence, CHOL is a "complementarily shaped lipid," while DOPE is not.

Figure 3:
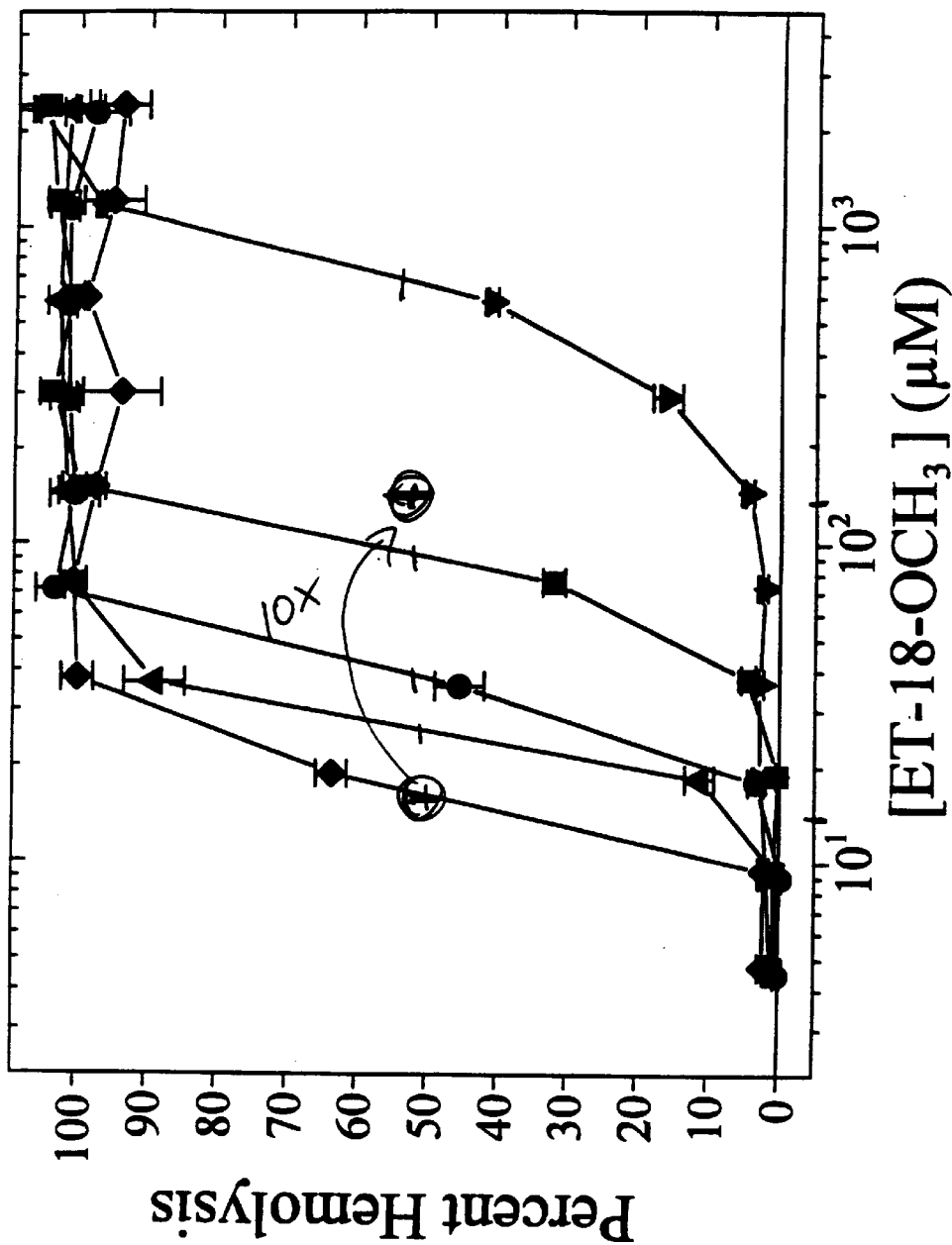
FIG. 3. Hemolytic activity of ET-18—OCH$_3$ incorporated in liposomes formed by extrusion through a 100 nm pore size filter. Symbols represent free ET-18—OCH$_3$ (♦), and ET-18—OCH$_3$ incorporated at 40 mole percent into liposomes with the lipids POPC (●), DOPC (filled ▲), DOPE (■), and cholesterol (filled ▽▽. Each preparation was run in triplicate, and the error bars represent S. D. Liposome size was measured by dynamic light scattering and found to be approximately 40 nm for samples except ET-18—OCH$_3$/cholesterol liposomes, which had a mean diameter of 77 nm.

The hemolytic activity of ET-18—OCH$_3$/CHOL, DOPE, POPC or DOPC liposomes, prepared as described below in Example 2, have also been examined, as described hereinbelow in Example 3. Results, presented hereinbelow in FIG. 3, are in the form of the ET-18—OCH$_3$ concentration in the various liposomes required to achieve hemolysis of 50% of the red blood cells present in a sample culture medium (H$_{50}$). The data indicate that for ET-18—OCH$_3$/cholesterol liposomes, the H$_{50}$ value was 661 $\mu$M (micromolar), that is, an etherlipid concentration of 661 micromoles was required in the medium in order for 50% of the RBCs present to be lysed. ET-18—OCH/DOPE liposomes exhibited an H$_{50}$ of 91 $\mu$M, i.e., were over 7 times more hemolytic than the ET-18—OCH$_3$ liposomes; ET-18—OCH$_3$/DOPC and ET-18—OCH$_3$/POPC liposomes had H$_{50}$ values of 38 and 26 $\mu$M, respectively. Thus, combination of glycerolipids and complementarily shaped lipids in liposomes significantly reduced the glycerolipids' hemolytic potential, and consequently enhanced their therapeutic usefulness, in comparison to glycerolipid/noncomplementary lipid liposome combinations Glycerolipids and complementary shaped lipids are combined in the lamellar lipid components of lipid-based carriers. Preferably, the carrier is a liposome, which is a self-assembling structure having either a single lipid bilayer (unilamellar liposome, "ULV"), or multiple lipid bilayers (multilamellar liposomes, "MLV"). Preferably, the liposome of this invention is either a multilamellar liposome, or a unilamellar liposome having an average size of about 25–200 nm.

Liposomes can be made by a variety of methods (for a review, see, for example, Deamer and Uster (1983)). These methods include without limitation: Bangham's method for making multilamellar liposomes (MLVs); Lenk's, Fountain's and Cullis' methods for making MLVs with substantially equal interlamellar solute distribution ("SPLVs;" see, for example, U.S. Pat. Nos. 4,522,803, 4,588,578, 5,030,453, 5,169,637 and 4,975,282); and Papahadjopoulos et al.'s reverse-phase evaporation method (U.S. Pat. No. 4,235,871) for preparing oligolamellar liposomes ("REVs"). ULVs can be produced from MLVs by such methods as sonication (see Papahadjopoulos et al. (1967)) or extrusion (U.S. Pat. Nos. 5,008,050 and U.S. Pat. No. 5,059,421). The liposome of this invention can be produced by the methods of any of these documents, the contents of which are incorporated herein by reference.

Various methodologies, such as sonication, homogenization, French Press application and milling can be used to prepare liposomes of a smaller size from larger liposomes. Extrusion (see U.S. Pat. No. 5,008,050) can be used to size reduce liposomes, that is to produce liposomes having a predetermined mean size by forcing the liposomes, under pressure, through filter pores of a defined, selected size. Tangential flow filtration (see WO89/008846), can also be used to regularize the size of liposomes, that is, to produce liposomes having a population of liposomes having less size heterogeneity, and a more homogeneous, defined size distribution. Liposome sizes can be determined by a number of readily practiced techniques, such as quasi-electric light scattering, and with equipment, e.g., Nicomp® particle sizers. The contents of the above-cited documents are incorporated herein by reference.

Moreover, liposomes of this invention can be dehydrated, stored and then reconstituted such that a substantial portion of its contents are retained. Liposomal dehydration generally requires use of a hydrophilic drying protectant such as a disaccharide sugar, e.g., sucrose or maltose, at both the inside and outside surfaces of the liposome bilayers (see U.S. Pat. No. 4,880,635, the contents of which are incorporated herein by reference). This hydrophilic compound is generally believed to prevent the rearrangement of the lipids in the liposome, so that the size and contents are maintained during the drying procedure and through subsequent rehydration. Appropriate qualities for such drying protectants are that they be strong hydrogen bond acceptors, and possess stereochemical features that preserve the intramolecular spacing of the liposome bilayer components. Alternatively, the drying protectant can be omitted if the liposome preparation is not frozen prior to dehydration, and sufficient water remains in the preparation subsequent to dehydration.

Liposomes of this invention can contain one or more additional bioactive agents, that is, one or more bioactive agents in addition to the bioactive glycerolipid. "Bioactive agents" are any compounds or compositions of matter which can be administered to animals. These include agents having biological activity in the animals, as well as those useful for imaging or other forms of diagnosis. Bioactive agents include, but are not limited to: antiviral, antibacterial, antifungal, antiparasitic, antimetabolic, antiglaucomic, anti-inflammatory or antineoplastic compounds, carbohydrates, amino acids, peptides, proteins, immunoglobulins, immunomodulators, dyes, toxins, enzymes, hormones, neurotransmitters, glycoproteins, radiolabels, radiopaque compounds, fluorescent compounds, cell receptor proteins, cell receptor ligands, mydriatic compounds, vasodilators, bronchodilators, local anesthetics, growth promoting agents, regenerative agents and the like.

Liposomes can be loaded with one or more biologically active agents by solubilizing the agent in the lipid or aqueous phase used to prepare the liposomes. Alternatively, ionizable bioactive agents can be loaded into liposomes by first forming the liposomes, establishing an electrochemical potential, e.g., by way of a pH gradient, across the outermost liposomal bilayer, and then adding the ionizable agent to the aqueous medium external to the liposome (see Bally et al. U.S. Pat. No. 5,077,056 and WO86/01102, the contents of which are incorporated herein by reference). Preferably, the additional bioactive agent is an anti-inflammatory or anti-cancer agent.

Also provided herein are compositions containing the carrier of this invention, e.g., compositions also containing a pharmaceutically acceptable carrier. Such carriers are generally acceptable for use in connection with the administration of therapeutic or diagnostic agents to animals. Pharmaceutically acceptable carriers are formulated according to a number of factors well within the purview of the ordinarily skilled artisan to determine and account for, including without limitation: the particular agent being administered, as well as its concentration, stability and intended bioavailability; the disease, disorder or condition being treated or diagnosed with the composition; the subject, its age, size and general condition; and the composition's intended route of administration, e.g., nasal, oral, ophthalmic, topical, transdermal, vaginal, subcutaneous, intramammary, intraperitoneal, intravenous, or intramuscular (see, for example, Nairn (1985)). Typical pharmaceutically acceptable carriers used in parenteral bioactive agent administration include, for example, D5W, an aqueous solution containing 5% weight by volume of dextrose, and physiological saline. Pharmaceutically acceptable carriers can contain additional ingredients, for example those which enhance the stability of the active ingredients included, such as preservatives and anti-oxidants.

Compositions of this invention can be administered to mammals by any of the standard means generally accepted in the art for doing so. Routes of administration, e.g., intravenous, intra-arterial, subcutaneous, intramuscular or intraperitoneal administration, are chosen with regard to a number of factors well within the purview of ordinarily skilled artisans, given the teachings of this invention, to determine and account for. Such factors include, without limitation: the age, body mass and general health of the subject being treated; the intended bioavailability of the drug; the particular form of disease being treated; the carrier used; and, the dose of therapeutic agent administered.

As described hereinabove, the glycerolipids of this invention can be therapeutically effective anticancer agents. Provision of the glycerolipids in combination with complementarily shaped lipids, in lamellar form, allows the glycerolipids' detergent-like activity to be directed against tumors while shielding normal cells, e.g., red blood cells, from adverse effect. Accordingly, compositions of this invention can be used in the treatment of mammals, e.g., humans, by reducing the size of tumors therein through the administration of an amount of a composition which comprises an effective amount of the glycerolipid.

An "effective amount" of a glycerolipid is any amount of the lipid effective to reduce the size of a tumor in mammals to which the glycerolipid has been administered. Effective amounts are generally chosen in accordance with a number of factors, e.g., the age, size and general condition of the subject, the cancer being treated and the intended route of administration, and determined by a variety of means, for example, dose ranging trials, well known to, and readily practiced by, ordinarily skilled artisans given the teachings of this invention. Typically, the effective amount of the glycerolipid is from about 1 mg per kg of the subject's body weight to about 1000 mg/kg.

Cancers treatable with the composition of this invention, through reductions in the size of tumors, include, without limitation leukemias, lymphomas, sarcomas and carcinomas, as well as brain, breast, stomach, prostate, colon and ovarian cancers. One or more additional bioactive agent(s), that is one or more biologically active agents in addition to the glycerolipid, can also be administered to animals treated with the pharmaceutical composition according to the practice of this invention. Such additional bioactive agents can be administered either separately from the glycerolipid/complementarily shaped lipid, or as part of the same composition that contains these lipids.

This invention will be better understood from the following Examples. However, those of ordinary skill in the art will readily understand that these examples are merely illustrative of the invention as defined in the claims which follow thereafter.

EXAMPLES

Example 1

Mean Molecular Area per Molecule ("MMAM") Measurement

The mean molecular area per molecule of formulations containing the etherlipid ET-18—$OCH_3$ was determined using a Langmuir-Blodgett mini-trough equipped with a dual barrier mechanism and a Wilhelmy balance, all obtained from KSV Instruments (Trumbull, Conn.). ET-18—$OCH_3$ formulations were prepared from lipid powders that were dissolved in a solvent system of hexane:ethanol 9:1. Single lipid solutions and mixtures were made to contain an overall lipid concentration of approximately 1.5 mM which was quantitated precisely by phosphate (Chen et al., 1956) and cholesterol assays (Rudel & Morris, 1973). Monolayers were formed by drop wise addition of sample on to the aqueous surface (10 mM HEPES, 150 mM NaCl buffer, pH 7.2) at the center of the trough. Sample was added until the surface pressure just started to rise above zero, at which time the exact volume of sample added was recorded. After waiting three minutes for solvent evaporation and monolayer stabilization, the surface area of the monolayer was reduced at a rate of 15 $cm^2$/min, and surface pressure was recorded. The solution level was maintained 1 mm below the top edge of the trough to avoid leakage; contact was maintained with the barriers (composed of Delrin) due to their hydrophilic nature.

Figure 1:
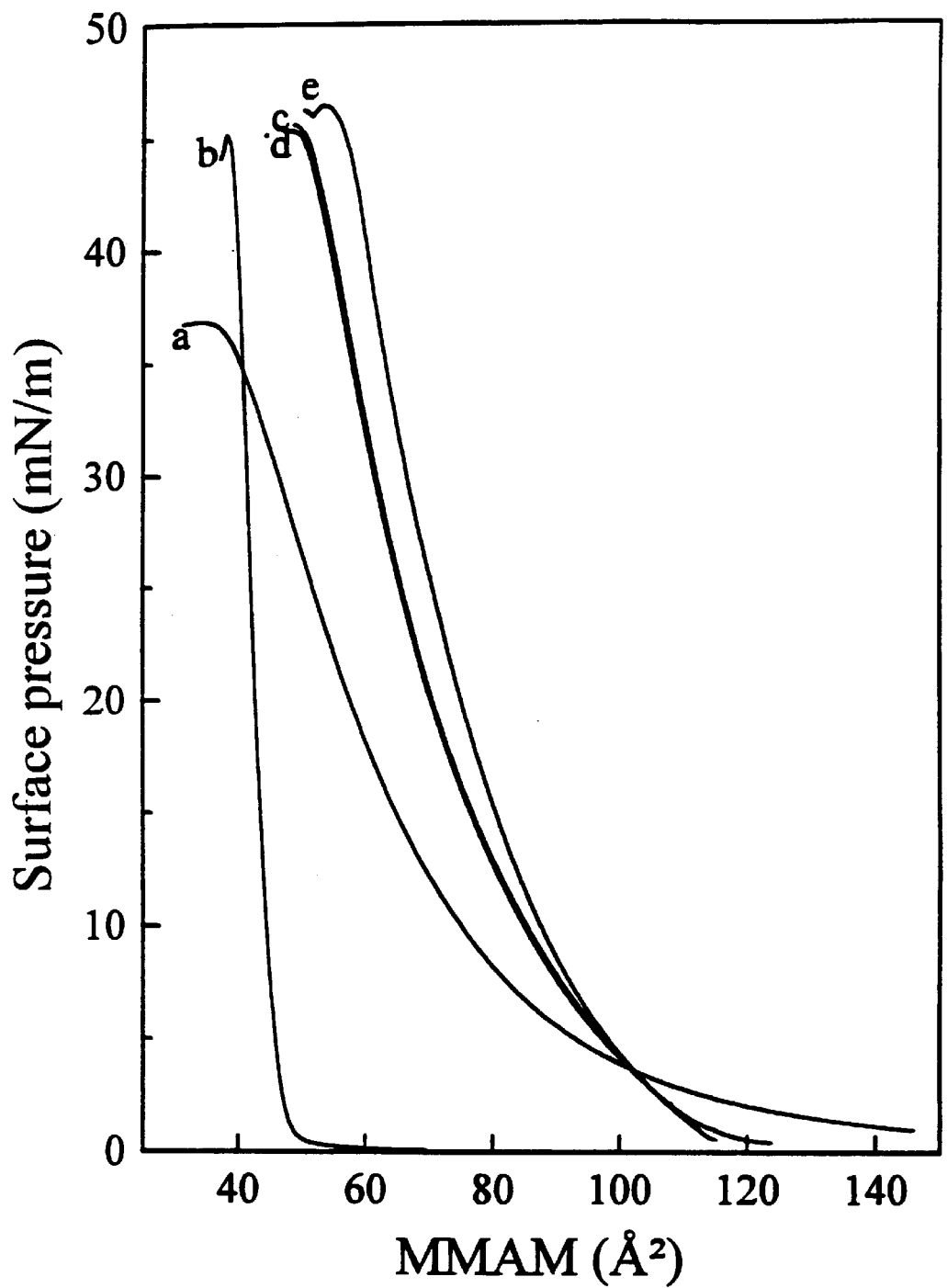
FIG. 1. Surface pressure versus mean molecular area per molecule ("MMAM") for monolayer films of individual lipids. Lipids are ET-18—OCH$_3$ (a), cholesterol (b), POPC (c), DOPC (d), and DOPE (e). Films were compressed at 15 cm$^2$/minute. Each curve is the average of three compressions.

Pressure vs. area curves were compiled from data obtained as described above (see FIGS. 1 and 2), and MMAM values were determined by extrapolating the steepest portion of the curve to the value at zero surface pressure. The highest collapse pressure measured for any lipid in this study ($\leq 47$ mN/m) was well below the values attained with disaturated PC molecules (>62 mN/m) indicating that the collapse pressure was not an artifactual consequence of a technical limitation. All experiments were done at 23° C. Area versus surface pressure profiles were obtained for combinations of EL-18 and the lipids cholesterol, POPC, DOPC or DOPE. Cholesterol and DOPE both have an inverted cone shape; it has previously been shown, with NMR and X-ray studies, that CHOL and DOPE form lamellar phase structures when mixed with the cone-shaped lipid lyso-PC (see Rand et al., 1975; Madden & Cullis, 1982; Wu et al., 1991). As the surface area was reduced, surface pressure increased as the lipids packed into an organized oriented monolayer, each characteristic for that lipid; at high surface pressure, the monolayers collapsed. MMAMs ($A_0$) were determined for each lipid by extrapolation of the steepest portion of the curves to the value at zero surface pressure; and are as follows: ET-18—$OCH_3$: 72.8 $Å^2$; CHOL: 44.8 $Å^2$; DOPE: 82.3 $Å^2$; POPC: 82.0 $Å^2$; and, DOPC: 82.0 $Å^2$.

Figure 2:
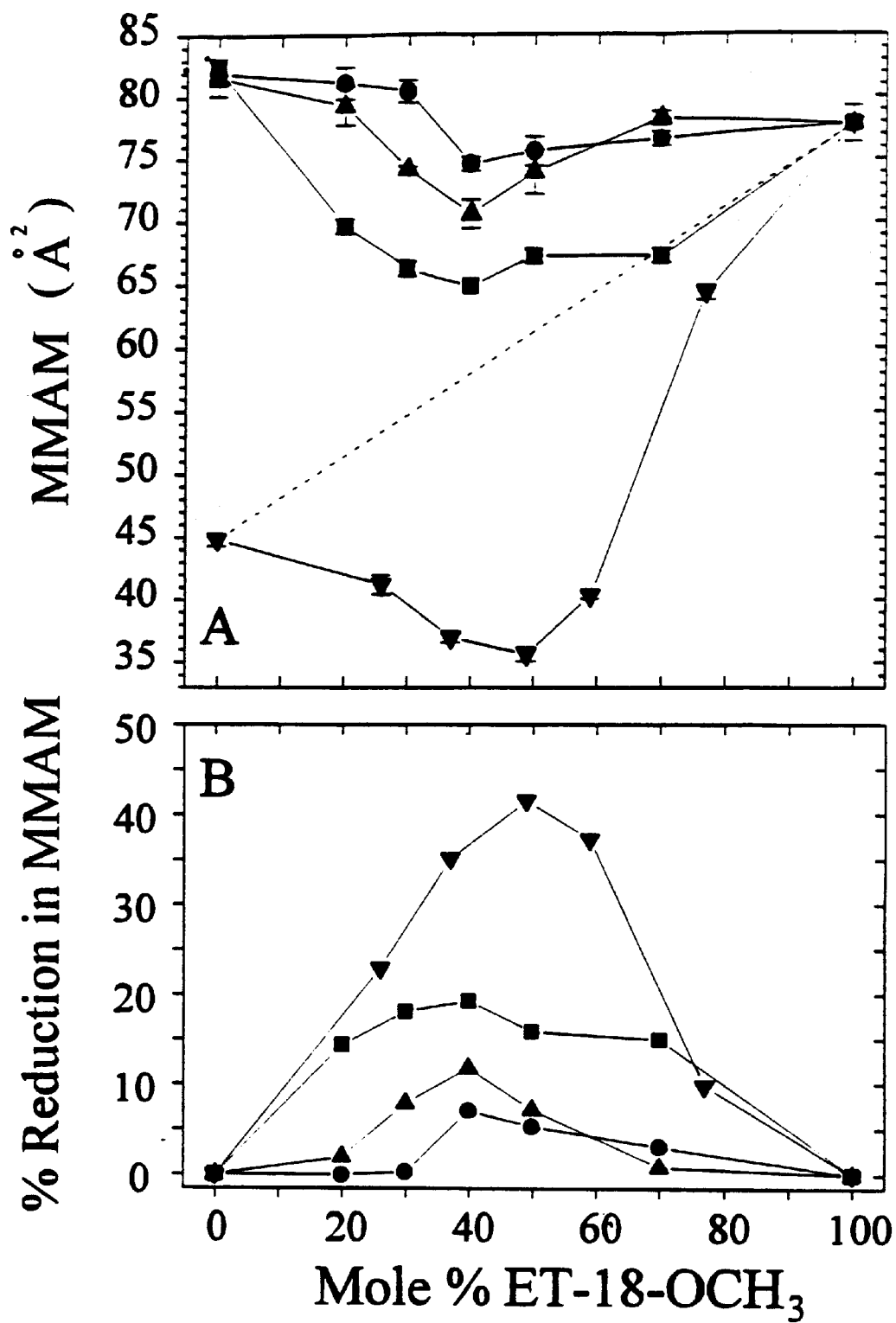
FIG. 2. A) Mean molecular area per molecule as a function of ET-18—OCH$_3$ content where monolayers were formed from ET-18—OCH$_3$ mixed with DOPC (●), POPC (filled ▲), DOPE (■), or cholesterol (filled ▽). Data are the average of 3 experiments, ±S.D. The dashed line represents the expected values (A$_0$) for cholesterol/ET-18—OCH$_3$ mixtures based on simple additivity of the individual MMAM values. B) Percent reduction in MMAM as a function of ET-18—OCH$_3$.

MMAM values of combinations of ET-18—$OCH_3$ with CHOL, DOPE, POPC and DOPC, at various mole percentages of each lipid, were obtained from the surface area-vs.-pressure curves shown in FIG. 2. The order for the percent reductions in MMAM values for the various ET-18—$OCH_3$/ lipid combinations was cholesterol>>DOPE>POPC>DOPC. MMAM reductions afforded the lipid combination by DOPE were, at most, less than 20%. However (see FIG. 3A), a 1:1 ET-18—OCH$_3$/CHOL combination had an actual MMAM ~25 Å$^2$ less than the expected value (represented in the figure by the dashed line). The much larger reduction afforded the lipid combination by cholesterol, as compared to DOPE, was surprising given that both cholesterol and DOPE have an inverted cone-shape.

Example 2

Liposome Preparation

All phospholipids were purchased from Avanti Polar Lipids (Alabaster, Ala.). Cholesterol was purchased from Sigma Chemical Co. (St. Louis, Mo.); all lipids and reagents used were of the highest purity available. Liposomes were prepared by first mixing the appropriate lipids in solvent, drying the lipid to a thin film using vacuum rotary evaporation, and hydrating the resulting film with buffer solution (10 mM HEPES, 150 mM NaCl, pH 7.4). The resulting dispersions were used without further processing for NMR studies. For hemolysis studies, the lipid dispersions were then repeatedly extruded through polycarbonate Nucleopore® membranes (Nuclepore Corp., Pleasanton, Calif.) of defined pore size. Liposomes were first passed 10 times through a membrane of 0.2 μm pore size and then 10 passes through a membrane of 0.1 μm pore size. For ET-18—OCH$_3$/cholesterol, the mixtures were first passed through a 0.4 μm pore size filter 10 times before proceeding to the 0.2 μm pore size filter and finally the 0.1 μm pore size filter. Liposome size was determined by quasi-elastic light scattering using a Nicomp® Model 270/370 Submicron Particle Sizer from Pacific Scientific (Menlo Park, Calif.).

First, the phosphorus NMR signal of hydrated hand-shaken dispersions for the ET-18—OCH$_3$/lipid systems was examined to confirm the existence of lamellar phase (see FIG. 2). The phosphorus NMR spectra for ET-18—OCH$_3$ at 40 mole % with both cholesterol and DOPE at 23° C. and 37° C., were typical of lamellar phase lipid (Gruner, 1992). For DOPC and POPC mixtures with ET-18—OCH$_3$, there was an additional isotropic component on top of the broader lamellar signature. The spectrum resembled that for mixtures of small and large liposomes (Hope et al., 1986) and the line width appeared to be too broad (3.6–3.9 ppm at half height) to be ET-18—OCH$_3$ micelles (Kumar et al., 1988). In order to determine whether this component was due to mixed micellar structures or small vesicular structures, the fraction that would not form a plug on top of the solution (the mixtures floated) upon centrifugation was collected, and the ratio of ET-18—OCH$_3$ to lipid was examined by TLC (as described below in Example 5). The ratios were essentially the same as that for the bulk sample indicating that the structures were small liposomes, and not ET-18—OCH$_3$-rich micellar structures.

Example 3

Hemolysis

Liposomes containing 40 mole % ET-18—OCH$_3$ were prepared as described in Example 2. All liposomes were extruded, in order to assure uniform size distribution. Extrusion was more difficult (higher pressure required) for the ET-18—OCH$_3$/cholesterol mixture, which had a final size distribution (77 nm) that was slightly larger than that for the other samples (40 nm); however, the ratio of lipids in the final preparation was not different from that found prior to extrusion.

Hemolysis was assessed as previously described (Perkins et al., 1992). Briefly, each sample was serially diluted with buffer solution and 0.3 ml of each diluted solution was mixed with 0.3 ml of washed human red blood cells [4% in PBS (v/v)]. For controls, 0.3 ml of the red blood cell suspension was mixed with either 0.3 ml of buffer solution (negative hemolysis control) or 0.3 ml of distilled water (positive hemolysis control). Samples and standards were placed in a 37° C. incubator and agitated for 20 hours. Tubes were centrifuged at low speed (2000 g) for 10 minutes to pellet RBCs. Two hundred μl of the supernatant was removed and mixed with 1 ml of water. Hemolysis was quantitated by absorbance at 550 nm using a Shimadzu 2101 UV-Vis Scanning Spectrophotometer (Shimadzu Corp., Kyoto, Japan). One hundred percent hemolysis was defined as the maximum amount of hemolysis obtained from free ET-18—OCH$_3$.

FIG. 3 displays the hemolysis profiles for the four ET-18—OCH$_3$ liposome preparations, as well as for free ET-18—OCH$_3$. Hemolysis was least for the ET-18—OCH$_3$/cholesterol liposomes, with the concentration of ET-18—OCH$_3$ that yielded 50% hemolysis ($H_{50}$) being 661 μM. This formulation was over 7 times less hemolytic than the ET-18—OCH$_3$/DOPE liposomes, in which the $H_{50}$ of ET-18—OCH$_3$ was 91 μM. The ET-18—OCH$_3$/DOPC and ET-18—OCH$_3$/POPC formulations exhibited similar $H_{50}$ values (38 and 26 μM, respectively); the $H_{50}$value for free ET-18—OCH$_3$ was (16 μM). Hemolytic activity of ET-18—OCH$_3$ small unilamellar liposomes ("SUVs") formulated at 40 or 60 mole % with cholesterol was compared. The 60 mole % ET-18—OCH$_3$ SUVs were as hemolytic as free EL-18—OCH$_3$. This confirmed our suspicion that ET-18—OCH$_3$, like lyso-PC (Kumar, 1991; Kumar et al., 1988), does not form stable liposome structures above a 1:1 stoichiometry.

Example 4

Phosphorus Nuclear Magnetic Resonance (NMR) Spectroscopy

Spectra were obtained at 121.51 MHz on a Bruker AC300 NMR Spectrometer (Bruker Instruments, Billerica, Mass.) at either 23° C. or 37° C. 16K points were acquired with a sweep width of 50 kHz using a 6 microsecond pulse. The average of 3000 acquisitions was processed with 50 Hz line broadening. Liposome samples were made by hydrating dried films of mixed lipids (see above). For NMR, ET-18—OCH$_3$ purchased from Alexis Corp. (San Diego, Calif.) was used. Samples contained a total of 20 mg/ml of ET-18—OCH$_3$ (approximately 60 mg/ml total lipid) except for the ET-18—OCH$_3$/cholesterol mixtures which contained 40 mg/ml ET-18—OCH$_3$ (60–90 mg/ml total lipid).

Figure 5:
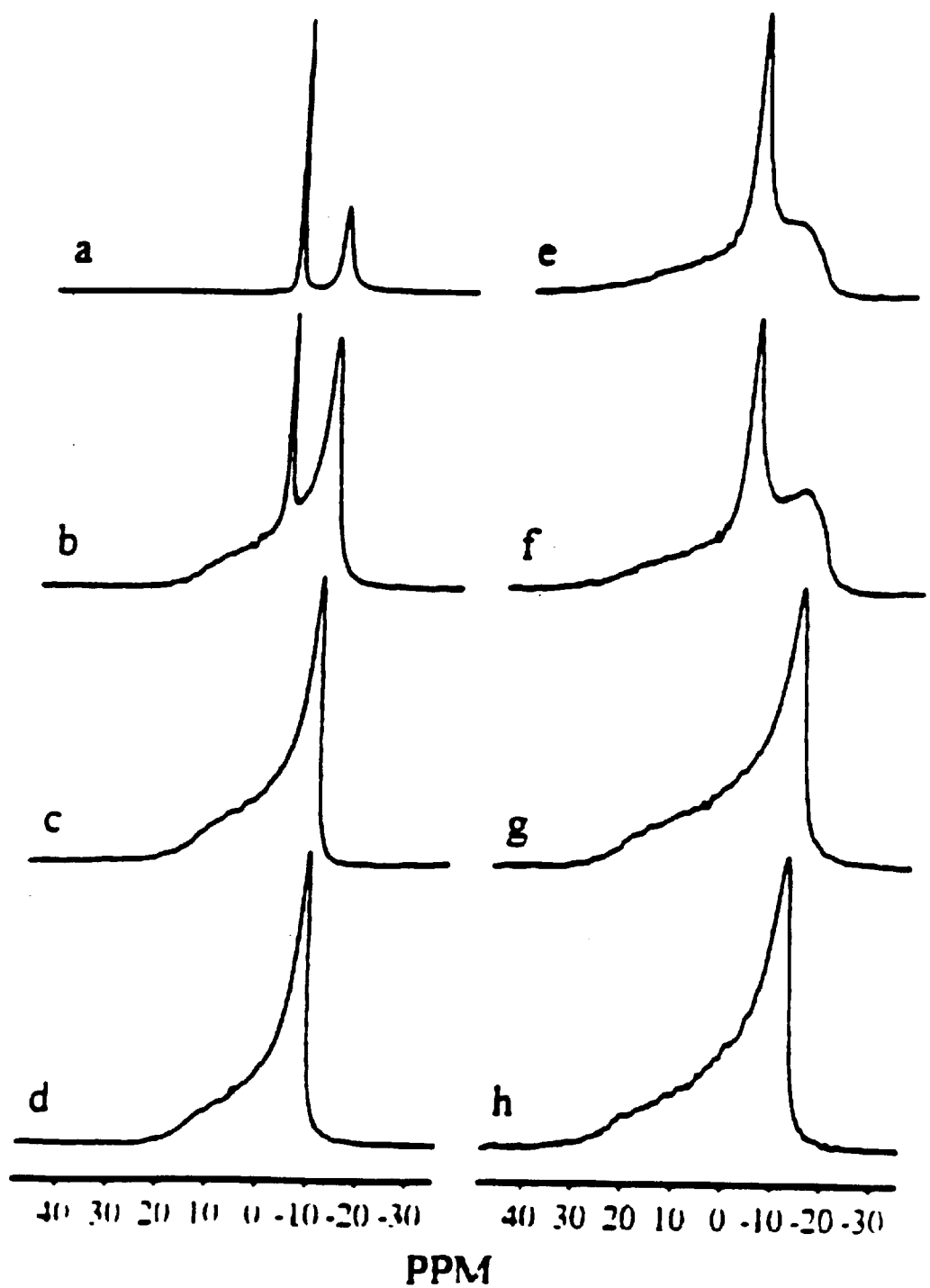
FIG. 5. Phosphorous NMR of ET-18—OCH$_3$ mixtures at various mole ratios with other lipids (x-axis: ppm): (a) ET-18—OCH$_3$/CHOL (60:40 mole ratio) at 23 deg. C.; (b) ET-18—OCH$_3$/CHOL (50:50 mole ratio) at23 deg. C.; (c) ET-18—OCH$_3$/CHOL (40:60 mole ratio) at23 deg. C.; (d) ET-18—OCH$_3$/CHOL (40:60 mole ratio) at 37 deg. C.; (e) ET-18—OCH$_3$/POPC (40:60 mole ratio) at 23 deg. C; (f) ET-18—OCH$_3$/DOPC (40:60 mole ratio) at 23 deg. C.; (g) ET-18—OCH$_3$/DOPE (40:60 mole ratio) at 23 deg. C.; (h) ET-18—OCH$_3$/DOPE (40:60 mole ratio) at 37 deg. C. The isotropic peak of (a) was assigned the value of 0 ppm.

The results (see FIG. 5) of phosphorous NMR studies of ET-18—OCH$_3$ at a 40 mole percent concentration with both cholesterol and DOPE, at 23 deg. C. and at 37 deg. C., demonstrated that the lipids were in the lamellar phase. For DOPC and POPC mixtures with ET-18—OCH$_3$, there was an additional isotropic component on top of the broader lamellar signature.

Example 5

Thin Layer Chromatography (TLC)

Aqueous samples were first mixed with methanol and chloroform in the ratio 0.8:2:1 to form a single monophase. An aliquot of this was then applied to a silica gel plate which was run in chloroform/methanol/water (65:25:4) and then developed with iodine vapor. Standards of each lipid were also run.

REFERENCES

Bazill, et al., "Role of Endocytosis in the Action of Ether Lipids on WEHI-3B, HL60, and FDCP-Mix A4 Cells", Cancer Research, 50, 7505–7512, Dec. 1, 1990

Berdel, "Ether Lipids and Derivatives as Investigational Anticancer Drugs", Onkologie 1990: 13:245–250

Bhatia, et al., "Stereospecific Synthesis of Antitumor Active Thioether PAF Analogs", Lipids, 26(12), 1424–1430, 1991

Chen, et al., "Microdetermination of Phosphorus", Anal. Chem.,28 (11), 1756–1758; 1956

Deamer, et al., "Liposome Preparation: Methods and Mechanisms", in *Liposomes*, Marcel Dekker, ed. M. Ostro, 1983, 27–51

Dietzfelbinger, et al., "Removal of Breast Cancer Cells from Bone Marrow by in Vitro Purging with Ether Lipids and Cryopreservation", Cancer Research 53, 3747–3751, Aug. 15, 1993

Gruner, "Nonlamellar Lipis Phases", in *The Structure of Biological Membranes*, 1992, CRC Press, ed. P. Yeagle, Buffalo, N.Y., pp 222–223

Kumar, et al., "Phosphlipid Deitribution and Headgroup Motion in Phosphatidylcholine Liposomes of Different Size", Biophys. J., 53, 1988, 121a Layton, et al., "The Interaction of Liposomes with Cells: The Relation of Cell Specific Toxicity to Lipid Composition", Eur J Cancer, 16, 1529–1538, 1980

Madden, et al., "Stabilization of bilayer Structure for Unsaturated Phosphatidylethanolamines by Detergents", BBA, 684 (1982), 149–153

Nairn, et al., "Solutions, Emulsions, Suspensions and Extractives", in *Pharmaceutical Sciences,* 1985, Mack Publishing Co., Easton, Pa.

Papahadjopoulos, et al. "Phospholipid Model Membranes, I. Structural Characteristics of Hydrated Liquid Crystals", BBA 135 (1967) 624–638

Powis, et al., "Selective Inhibition of Phosphatidyloinositol Phospholipase C by Cytotoxic Ether Lipid Analogues", Cancer Research 52, 2835–2840, May 15, 1992

Reed, et al., "Antineoplastic Ether-Linked Phospholipid Inudces Differentiation of Acute Myelogenous Leukemic KG-1 Cells Into Macrophase-Like Cells", Life Sciences, 49, 1221–1227, 1991

Runge, "Destruction of human Solid tumors by Alkyl Lysophospholipids", JNCI, 64(6), 6/1980, 1301–1306

Tritton, et al., "How to Kill Cancer Cells: Membranes and Cell signaling as Targets in Cancer Chemotherapy", Cancer Cells, April 1990, 95–105

Stedman's Medical Dictionary, pp 707–708

Stedman's Medical Dictionary, pp 123–124

Workman, "Antitumor Ether Lipids: Endocytosis as a Determinant of Cellular Sensitivity", Cancer Cells, 3(8), 315–317, August 1991

Workman, et al., "Platelet-activating factor (PAF) antagonist WEB 2086 does not modulate the cytotoxicity of PAF or antitumour alkyl lysophospholipids ET-18-O-Methyl and SRI 62-834 in HL-60 promyelocytic leukaemia cells", Biochemical Pharmacology, 41(2), 319–322,1991

Wu, et al., "Modified In Vivo behavior of Liposomes Containing Synthetic Glycolipids", BBA 674 (1981), 19–29

Zeisig, et al., "Antineoplastic activity in vitro of free an liposomal alkylphosphocholines", Anti-Cancer Drugs, 4, 57–64, 1993

What is claimed is:

1. A method of treating an animal afflicted with a cancer which comprises reducing the size of a cancerous tumor susceptible to the cytotoxic effects of an etherlipid, the method comprising the steps of administering to the animal a pharmaceutical composition comprising:
   (a) a pharmaceutically acceptable carrier; and,
   (b) a lipid-based carrier having a lipid component which consists essentially of:
      (i)) an etherlipid having the formula:

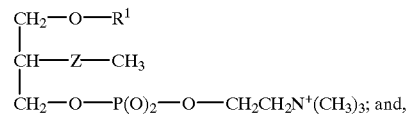

(ii) a complementarily shaped lipid,
wherein:
   $R^1$ is a group having the formula $Y_1Y_2$;
   $Y_1$ is $-(CH_2)_{n1}(CH=CH)_{n2}(CH_2)_{n3}(CH=CH)_{n4}(CH_2)_{n5}(CH=CH)_{n6}(CH_2)_{n7}(CH=CH)_{n8}(CH_2)_{n9}$;
   the sum of $n1+2n2+n3+2n4+n5+2n6+n7+2n8+n9$ is an integer of from 9 to 23;
   n1 is zero or an integer of from 1 to 23, n3 is zero or an integer of from 1 to 20, n5 is zero or an integer of from 1 to 17, n7 is zero or an integer of from 1 to 14 and n9 is zero or an integer of from 1 to 11;
   each of n2, n4, n6 and n8 is independently zero or 1;
   $Y_2$ is $CH_3$ or $CO_2H$;
   Z is oxygen or sulfur;
   the etherlipid comprises from about 30 mole percent to less than about 50 mole percent of the lipid component;
   the complementarily shaped lipid comprises from greater than about 50 mole percent to about 70 mole percent of the lipid component; and, the $MMAM_{actual}$ of the lipid is at least about 20% less than the $MMAM_{expected}$ of the lipid, and wherein the amount of the composition administered to the animal comprises a tumor growth-reducing effective amount of the etherlipid.

2. The method of claim 1, wherein the lipid-based carrier is a liposome.

3. The method of claim 1, wherein $R^1$ is $(CH_2)_{17}CH_3$.

4. The method of claim 3, wherein the etherlipid is:
CH —O—$(CH_2)_{17}CH_3$ 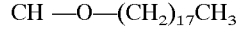

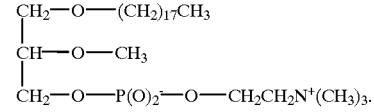

5. The method of claim 1, wherein the complementarily shaped lipid is cardiolipin, diarachidonoyl phosphatidylethanolamine, a neutral sterol or an anionic sterol derivative selected from the group consisting of sulfate, phosphate and organic dicarboxylic acid salt derivatives.

6. The method of claim 5, wherein the complementarily shaped lipid is the neutral sterol cholesterol.

7. The method of claim 5, wherein the complementarily shaped lipid is the anionic sterol derivative cholesterol sulfate.

8. The method of claim 5, wherein the complementarily shaped lipid comprises a neutral sterol and an anionic sterol derivative.

9. The method of claim 8, wherein the neutral sterol and anionic sterol derivative are present in the lipid at a respective molar ratio of about 5:1.

10. The method of claim 8, wherein the neutral sterol is cholesterol and the anionic sterol derivative is cholesterol sulfate.

11. The method of claim 1, wherein the etherlipid comprises about 40 mole percent of the lipid component and the complementarily shaped lipid comprises about 60 mole percent of the lipid component.

12. The method of claim 1, wherein the etherlipid is

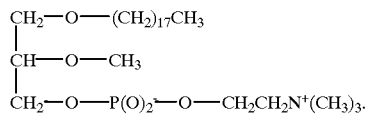

and wherein the complementarily shaped lipid is cholesterol, cholesterol sulfate or a 5:1 molar combination of cholesterol and cholesterol sulfate.

13. The method of claim 12, wherein the etherlipid comprises about 40 mole percent of the lipid component and the complementarily shaped lipid comprises about 60 mole percent of the lipid component.

14. The method of claim 2, wherein the liposome is a unilamellar liposome having an average size of about 50–250 nm.

15. The method of claim 1, wherein the tumor growth-reducing effective amount of the etherlipid is from about 1 mg of the etherlipid per kg of the animal's body weight to about 1000 mg per kg.

16. The method of claim 1, wherein the cancer is a leukemia, lymphomas, sarcoma or carcinoma.

17. The method of claim 1, wherein the cancer is a brain, breast, prostate, colon, stomach or ovarian cancer.

18. The method of claim 1, comprising administering an additional bioactive agent to the animal.

* * * * *